United States Patent
Munenaka

(10) Patent No.: US 7,816,120 B2
(45) Date of Patent: Oct. 19, 2010

(54) TEMPERATURE CONTROLLER FOR STRUCTURE

(75) Inventor: Katsumi Munenaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1057 days.

(21) Appl. No.: 11/527,506

(22) Filed: Sep. 27, 2006

(65) Prior Publication Data

US 2007/0077647 A1    Apr. 5, 2007

(30) Foreign Application Priority Data

Oct. 4, 2005    (JP)    ............... 2005-291151

(51) Int. Cl.
  *C12M 1/36*  (2006.01)
  *C12M 1/38*  (2006.01)
  *C12M 3/00*  (2006.01)

(52) U.S. Cl. .............. 435/286.1; 435/286.5; 435/303.1; 435/293.1; 435/6

(58) Field of Classification Search ...................... 435/6, 435/286.1, 286.5, 287.3, 288.4, 293.1, 303.1, 435/305.1
See application file for complete search history.

(56) References Cited

U.S. PATENT DOCUMENTS

| | | | |
|---|---|---|---|
| 5,795,547 A * | 8/1998 | Moser et al. ................. | 422/104 |
| 6,509,186 B1 * | 1/2003 | Zou et al. ................. | 435/286.1 |
| 6,556,940 B1 * | 4/2003 | Tretiakov et al. ............ | 702/130 |
| 7,238,517 B2 * | 7/2007 | Atwood et al. ........... | 435/286.1 |
| 7,244,913 B2 | 7/2007 | Murakami et al. | |
| 2003/0008286 A1 * | 1/2003 | Zou et al. ....................... | 435/6 |
| 2004/0191896 A1 * | 9/2004 | Miao et al. ................ | 435/303.1 |
| 2007/0036679 A1 | 2/2007 | Munenaka .................. | 422/68.1 |
| 2007/0128644 A1 | 6/2007 | Munenaka ..................... | 435/6 |

FOREIGN PATENT DOCUMENTS

| | | |
|---|---|---|
| JP | 2005-40784 | 2/2005 |
| JP | 2005-269906 | 10/2005 |

* cited by examiner

*Primary Examiner*—Walter D Griffin
*Assistant Examiner*—Shanta G Doe
(74) *Attorney, Agent, or Firm*—Fitzpatrick, Cella, Harper & Scinto

(57) ABSTRACT

A temperature controller for controlling temperature of a first structure having a first flat face comprises a second structure having a second flat face for planar contact with the first flat face, a pressure-applying means for pressing the first structure, a second supporting means for supporting the second structure to be capable of changing inclination of the second flat face, a first supporting means for supporting the first structure by contact with a portion of the first structure other than the first flat face, and a temperature-controlling means, wherein the first structure is supported by pressing the first structure by the pressure-applying means, and the second structure is brought into contact with the temperature-controlling means with interposition of the second supporting means.

4 Claims, 6 Drawing Sheets

FIG. 4A
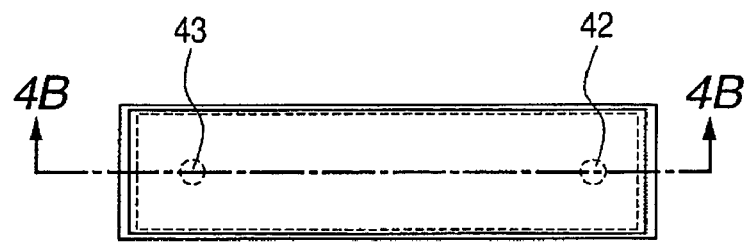
FIG. 4B
FIG. 4C
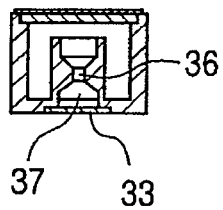 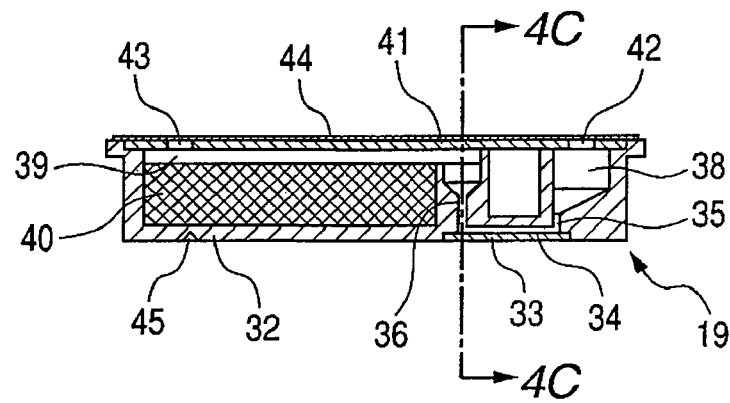
FIG. 4D
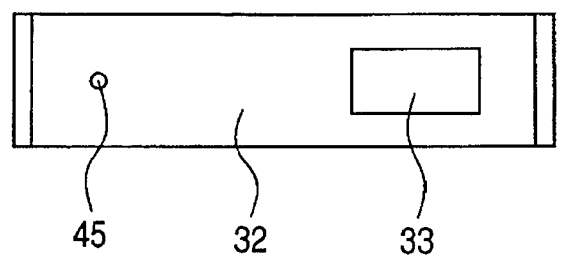

TEMPERATURE CONTROLLER FOR STRUCTURE

BACKGROUND OF THE INVENTION

1. Field of the Invention

The present invention relates to a temperature controller for controlling the temperature of a part of a structure such as a biochemical reaction cassette.

2. Description of the Related Art

For rapid and precise detection of a target nucleic acid in a nucleic acid sample and analysis of the nucleic acid base sequence, various methods are known which utilize a hybridization reaction with a probe carrier. The typical probe carrier for the hybridization reaction is a SNA microarray which immobilizes, on a bead or a glass plate, a probe having a base sequence complementary to the target nucleic acid.

This DNA microarray is promising for medical diagnosis for identifying a pathogen, and for genetic diagnosis for inspecting the physical feature of a patient. For practicing such diagnosis inspection, simplification of the operation is necessary for higher efficiency of the data analysis and examination. However, the inspection conducted with a probe bared on the surface of the immobilizing member can cause undesirable contact of a foreign object with the base plate of a microarray. This can cause defect or contamination of the probe, making difficult the precise inspection. Therefore, the operator should carefully handle the DNA microarray not to touch the base plate with a finger or the like. This may lower the efficiency of inspection. For higher efficiency of the analysis and inspection, several structures of biochemical reaction cassettes were disclosed, in which the microarray is placed in a reaction chamber to conduct the hybridization reaction in the reaction chamber and the detection is conducted thereafter.

During the hybridization reaction in such a biochemical reaction cassette, the temperature of the DNA microarray and the reaction chamber should be controlled at a prescribed temperature. The temperature can be controlled effectively by bringing a face of a heat-conducting member into contact with a face of the base plate of the DNA microarray.

FIG. 7 illustrates a known incubator device disclosed in Japanese Patent Application Laid-Open No. 2005-269906. The incubator device shown in FIG. 7 has reaction vessel 70, temperature controller 72, heat-conducting plate 100, and high-temperature-conducting sheet 102. For constituting the incubator device, firstly a heat-conductive plate having a temperature controller in contact with the lower face is placed horizontally, and thereon, high-temperature-conducting sheet 102 and reaction vessel 70 are placed in the named order. Heat insulation plate 80 is placed detachably on reaction vessel 80 to reduce the influence of outside temperature and to prevent contamination. The heat insulation plate is fixed by resin plate 84.

Box-shaped cover 90 is provided to cover heat insulation plate 80 and resin plate 84. Springs 92 are provided between cover 90 and resin plate 84. When the cover is closed, springs 92 apply pressure against the resin plate and through the heat insulation plate against reaction vessel 70 and to pressure-contact reaction vessel 10 with high-temperature conduction sheet 102.

With the above constitution, box-shaped cover 90 placed on the incubator device applies a pressure through springs 92 to the reaction vessel to strengthen the contact between the reaction vessel and the high-temperature conducting sheet to lower the contact thermal resistance and to increase the efficiency of heat conduction from temperature controller 72 to reaction vessel 70.

The incubator device disclosed in the above-mentioned Japanese Patent Application Laid-Open No. 2005-269906 is advantageous in heat conduction to the entire reaction vessel. However, in the case where the amount of the reactant is small and occupies only a part of the reaction vessel, the entire reaction vessel need not be temperature-controlled. In this case, uniform heating of the entire reaction vessel including a portion requiring no temperature control is inefficient in view of the heating efficiency.

Further, in use of the biochemical cassette, the flow rate of the solution in the reaction chamber should be precisely controlled during the biochemical reaction. For the flow rate control, the posture of the biochemical reaction cassette is preferably fixed to some extent during the biochemical reaction. When the above prior art technique is employed without modification, the biochemical reaction cassette is held directly by the elastic member, which makes it difficult to control precisely the posture of the biochemical reaction cassette.

In the case where a heat-conductive solid member is brought into direct contact with the biochemical cassette, care should be taken not to cause point contact of the heat-conductive solid member with a part of the structure to prevent nonuniform heat conduction.

From the above-mentioned consideration, for local heat control of the structure, the two measures below should be taken simultaneously:

(1) A pressure is applied to the biochemical cassette to bring the heat-conductive member for temperature control into face-to-face contact with a part of the structure; and (2) The biochemical reaction cassette is held with dynamic balance entirely to keep its posture.

To solve the above problems, the present invention intends to provide a temperature controller suitable for controlling a part of a biochemical reaction cassette.

The temperature controller is applicable not only for temperature control of the aforementioned biochemical reaction cassette but also widely for heating locally a general structure.

SUMMARY OF THE INVENTION

According to an aspect of the present invention, there is provided a temperature controller for controlling temperature of a first structure having a first flat face, comprising: a second structure having a second flat face for planar contact with the first flat face; a pressure-applying means for pressing the first structure; a second supporting means for supporting the second structure to be capable of changing inclination of the second flat face; a first supporting means for supporting the first structure by contact with a portion of the first structure other than the first flat face; and a temperature-controlling means, wherein the first structure is supported by pressing the first structure by the pressure-applying means, and the second structure is brought into contact with the temperature-controlling means with interposition of the second supporting means.

The second supporting means is preferably an elastic member, and the second structure is preferably a heat-conductive member having the second flat face and is supported through the elastic member being in contact with the temperature-controlling means.

The plural first structures are preferably in planar contact with the single second structure.

The first structure is preferably a biochemical reaction cassette for causing a biochemical reaction in the first structure. The first flat face of the biochemical reaction cassette is preferably a member for forming a wall face of the chamber for causing the biochemical reaction. The member for forming the wall face is preferably a DNA microarray.

The temperature controller preferably further contains a connecting member of a mechanism for control of the liquid flow in the biochemical reaction cassette.

According to another aspect of the present invention, there is provided a temperature controller for controlling temperature of a first structure having a first flat face, comprising: a second structure having a second flat face for planar contact with the first flat face; a pressure-applying means for pressing the first structure; a supporting means for supporting the first structure by contact with a portion of the first structure other than the first flat face; and a temperature-controlling means, wherein the second structure is elastic and supports the first structure by pressing the first structure with the pressure-applying means, and the second structure is in contact with the temperature-controlling means.

In the present invention, the shape of the surface of the structure is not limited to be planar, but may be stepped or curved.

According to the present invention, a first structure and a second structure are held in such a manner that inclination of a second flat face of the second structure relative to a first flat face of the first structure can be varied. Thereby, the first structure, when pressure is applied thereto, is brought surely into face-to-face contact with the second flat face of the second structure following the inclination of the second flat face of the second structure. Further, a supporting means are provided to be in contact with the portion of the first structure other than the first flat face to keep the posture of the first structure to some extent with dynamic balance. Thereby, the pressure is uniformly applied to the contact interface to enable sufficient heat conduction between the first structure and the second structure.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 4A, 4B, 4C and 4D illustrate a construction of a biochemical reaction cassette employed in the biochemical reaction apparatus of FIG. 1.

DESCRIPTION OF THE EMBODIMENTS

Preferred embodiments of the present invention will now be described in detail in accordance with the accompanying drawings.

Figure 1:
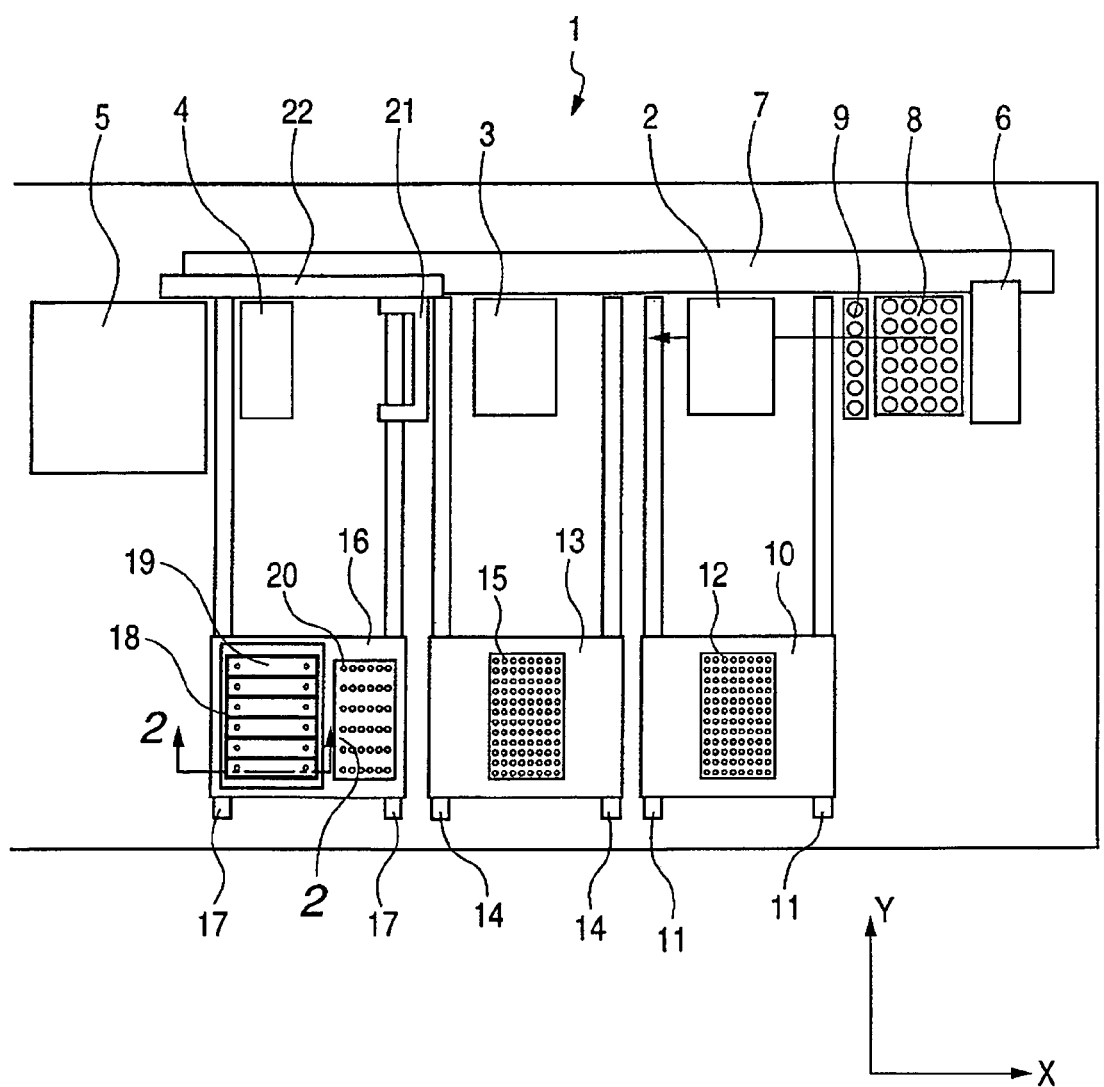
FIG. 1 is a plan view illustrating schematically a constitution of a biochemical reaction apparatus according to an example of the present invention.
Figure 2:
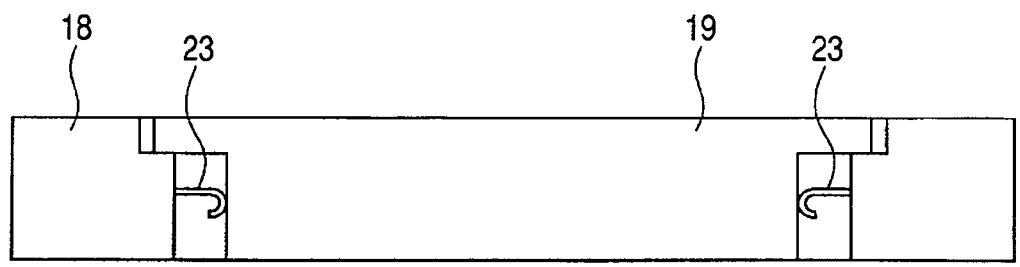
FIG. 2 is a sectional view taken along line 2-2 in FIG. 1.
Figure 3A:
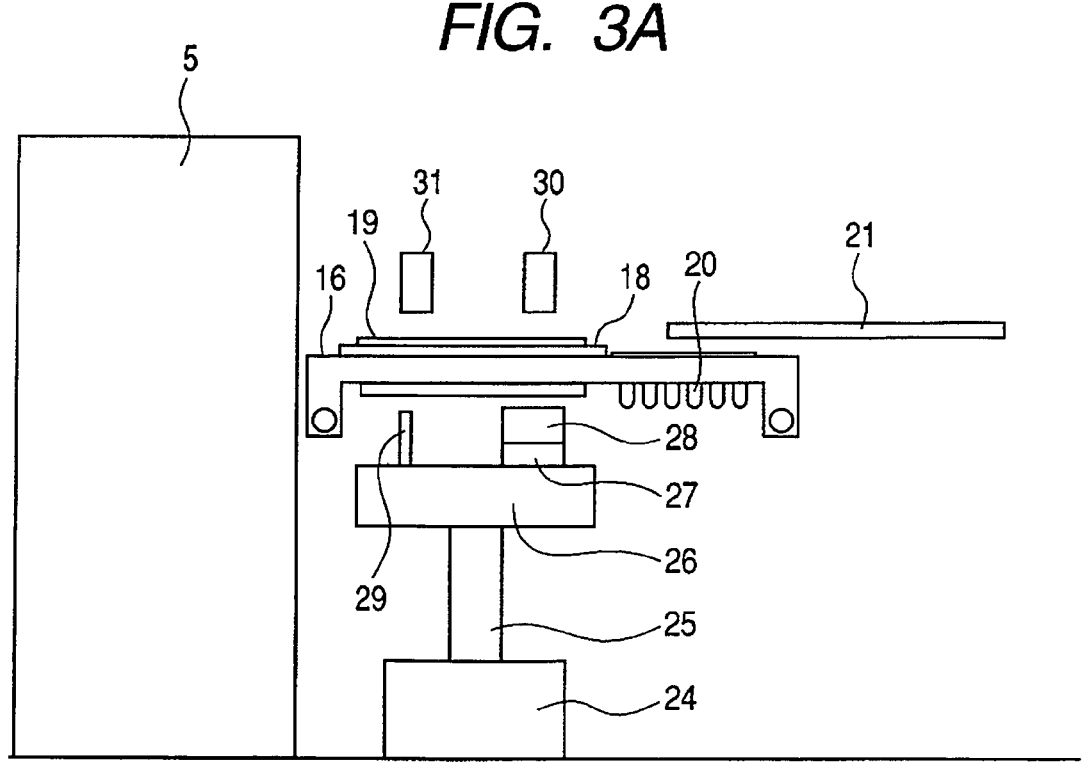
FIG. 3A is a front view of a hybridization section and the periphery thereof of the biochemical reaction apparatus shown in FIG. 1 before the hybridization reaction.
Figure 3B:
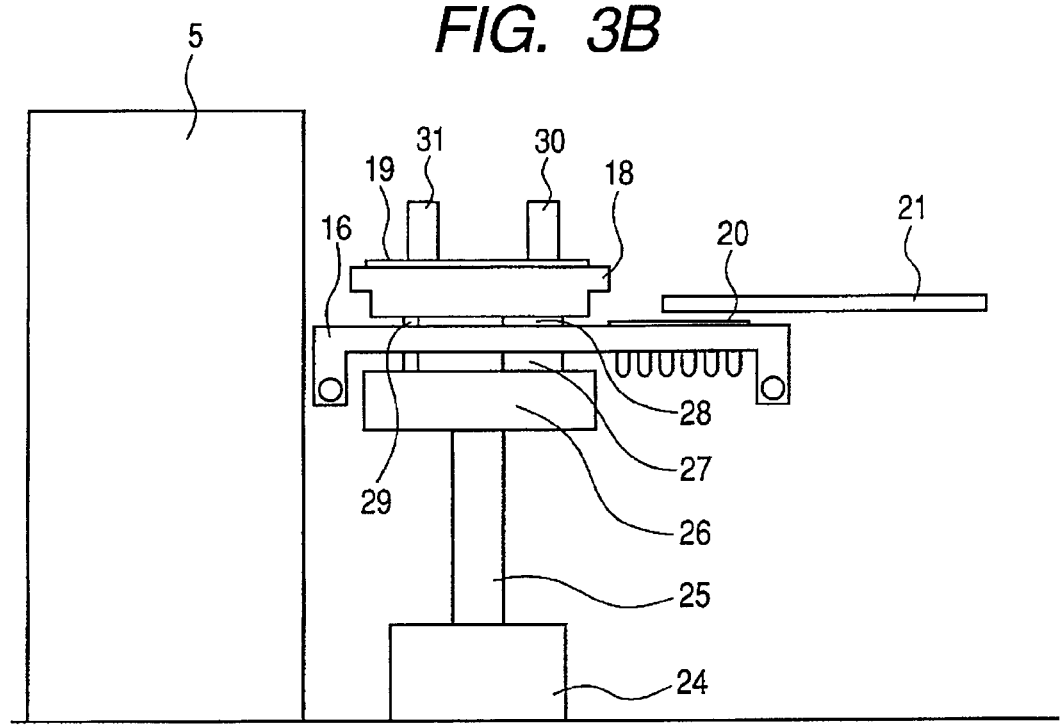
FIG. 3B is a front view of a hybridization section and the periphery thereof of the biochemical reaction apparatus shown in FIG. 1 during the hybridization reaction.
Figure 3C:
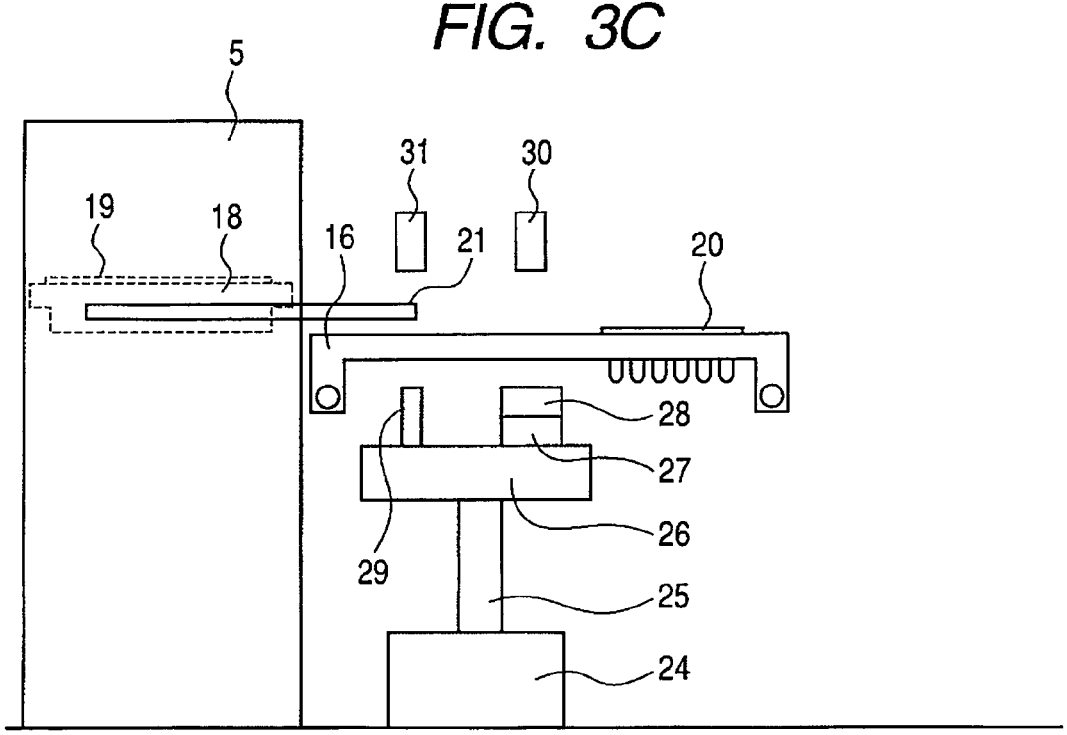
FIG. 3C is a front view of a hybridization section and the periphery thereof of the biochemical reaction apparatus shown in FIG. 1 after the hybridization reaction.

Firstly, the entire constitution of biochemical reaction apparatus of an embodiment of the present invention is explained by reference to FIGS. 1 to 3D. FIG. 1 is a plan view of the biochemical reaction apparatus. FIG. 2 is a sectional view taken along line 2-2 in FIG. 1. FIGS. 3A to 3C are front views of hybridization section 4 and periphery thereof shown in FIG. 1 in time series.

Biochemical reaction apparatus 1 of this embodiment is employed for detecting a target nucleic acid by use of a DNA microarray. The detection of a target nucleic acid by use of a DNA microarray is conducted generally through steps shown below.

In the first step, the target nucleic acid is amplified by a method typified by a PCR method. Specifically, a first primer and a second primer are added to the nucleic acid sample, and the mixture is subjected to a temperature cycle. The first primer bonds selectively to a part of the target nucleic acid, and the second primer bonds selectively to a part of a nucleic acid complementary to the target nucleic acid. The bonding of the double-stranded nucleic acid containing the target nucleic acid to the first and the second primers causes amplification of the double-stranded nucleic acid containing the target nucleic acid by elongation reaction. After sufficient amplification of the double-stranded nucleic acid containing the target nucleic acid, a third primer is added to the nucleic acid sample. The mixture is subjected to a temperature cycle. The third primer has been labeled by an enzyme, fluorescent substance, light-emitting substance, or the like, and bonds selectively to a part of the nucleic acid complementary to the target nucleic acid. The bonding of the third primer to the nucleic acid complementary to the target nucleic acid cause amplification of the target nucleic acid labeled by an enzyme, fluorescent substance, light-emitting substance, or the like by elongation reaction. As the result, in the presence of the target nucleic acid in the nucleic acid sample, the labeled target nucleic acid is formed, whereas in the absence of the target nucleic acid in the nucleic acid sample, the labeled target nucleic acid is not formed.

In the second step, this nucleic acid sample is brought into contact with a DNA microarray to cause hybridization reaction with the probe in the microarray. This step of initiation of the hybridization reaction includes temperature elevation of the DNA microarray and the nucleic acid sample. When the target nucleic acid complementary to the probe is present, hybridization occurs to form a hybrid of the probe and the target nucleic acid.

In the third step, the target nucleic acid is detected. For example, when the labeling substance is a fluorescent substance, the fluorescent substance is excited and the luminance is measured. Thus the formation of a hybrid of the probe and the target nucleic acid can be detected by the label of the target nucleic acid, and thereby the presence of a specific base sequence can be confirmed.

Biochemical reaction apparatus 1 of this embodiment is constituted to conduct, in addition to the above steps, extraction of the DNA which is an object of confirmation of the presence of the target nucleic acid. For conducting the above steps, the biochemical reaction apparatus 1 has extraction section 2, amplification section 3, hybridization section 4, and detection section 5 arranged in the named order in the X direction as shown in FIG. 1. Further, biochemical reaction apparatus 1 has also pipette tip holder 8 for holding pipette tips for handling a liquid such as the specimen or reagent; and sample holder 9 adjacent to the extraction section 2.

Biochemical reaction apparatus 1 has pipette unit 6 for handling a liquid with a pipette tip attached thereto. The pipette unit 6 is connected to pipette-driving shaft 7 extending in the X-direction in FIG. 1, and is movable over the range including pipette tip holder 8, sample holder 9, extraction section 2, amplification section 3, and hybridization section 4.

Further, biochemical reaction apparatus 1 has delivering carriers 10,13,16 which are movable respectively to extraction section 2, amplification section 3, or hybridization section 4 along delivery shafts 11,14,17 extending in Y-direction in FIG. 1. The delivering carriers 10,13,16 support reagent containers 12,15,20 for the reagents for the treatments.

Delivering carrier 16 for hybridization section 4 is provided with tray 18 for holding plural biochemical reaction cassettes (first structure) 19 explained later. Biochemical reaction cassette 19 is held by pressing members 23 so as not to come off readily from tray 18 as shown in FIG. 2. Incidentally, the manner of supporting biochemical reaction cassette 19 in tray 18 is not limited to that shown in FIG. 2, provided that the biochemical reaction cassette 19 is not readily disengaged from tray 18.

In hybridization section 4, below delivering carrier 16 as shown in FIGS. 3A to 3C, vertical motion stage 26 is provided which is driven vertically by motor 24 and vertical driving shaft 25. Vertical motion stage 26 has a bar-shaped supporting member (supporting means) 29 projecting upward, and Peltier element 27 and thermal block (a second structure) 28 placed thereon. Thermal block 28 may be made from a heat-conductive material like aluminum.

Supporting member 29 and thermal block 28 are brought into contact with biochemical reaction cassette 19 placed on delivering carrier 16, when vertical motion stage 26 is lifted. Thereby, as shown in FIG. 3B, biochemical cassette 19 is lifted together with tray 18. For contact with the upper face of biochemical reaction cassette 19, pressing mechanism 30 (energizing means) and connecting mechanism 31 are provided. Pressing mechanism 30 and connecting mechanism 31 may be supported movably by a vertical motion mechanism not shown in the drawing.

Being not shown in the drawings, plural supporting members 29 are provided for respective biochemical reaction cassettes 19. Thermal block 28, pressing mechanism 30, and connecting mechanism 31 may be provided respectively in plurality for plural biochemical reaction cassettes 19, or otherwise may be brought into contact simultaneously with plural biochemical reaction cassettes 19.

Delivery section 21 is placed at a suitable height for engaging with lifted tray 18. Delivery section 21 is connected to delivery guide 22 extending in X-direction in FIG. 1 from hybridization section 4 to detection section 5, and is movable along this delivery guide.

Next, the genetic inspection procedure is explained below.

Before the inspection, a necessary number of pipette tips are set in pipette tip holder 8, and inspection samples are placed in sample holder 9. Reagent containers 12,15,20 containing prescribed reagent are placed on delivering carriers 10,13,16. Biochemical reaction cassettes 19 supported on tray 18 are set on delivery carrier 16 corresponding to hybridization section 4.

To start the inspection, a specimen sample, a pipette tip, and reagent container 12 for extraction should be set at least in the apparatus. Therefore, biochemical reaction apparatus 1 may be designed to start the inspection immediately after the above objects are set therein. Otherwise, biochemical reaction apparatus 1 may be designed not to start the inspection unless reagent containers 15,20 and biochemical reaction cassette 19 supported by tray 18 are set in the apparatus.

On starting the inspection, firstly, delivering carrier 10 is moved to extraction section 2 for treatment of the extraction step. Then, pipette unit 6 is allowed to take up a fresh pipette tip to fit thereto from pipette tip holder 8, allowed to suck up the specimen sample from sample holder 9 into the pipette tip, moved to the position of extraction section 2, and allowed to discharge the specimen samples into reagent container 12. The prescribed treatment is conducted in the extraction section 2 to finish the extraction step. This treatment includes extraction and purification, and may include, for example, mixing of a reagent, and stirring. After completion of the extraction step, DNA extracted from the specimen sample is placed in reagent container 12. The pipette tips after use are discarded (not shown in the drawing). The pipette unit 6 takes up new pipette tip in the subsequent step for the treatment. The same operation is conducted in subsequent steps.

Next, for conducting the treatment of the amplification step, delivering carrier 13 is moved to amplification section 3. Pipette unit 6 sucks DNA, extraction-purification product, from reagent containers 12, and discharges them to reagent container 15. In reagent container 15, the prescribed treatment is conducted to complete the amplification treatment. The amplification treatment may include operations of mixing of the reagent, stirring, and temperature control. On completion of the amplification step, reagent containers 15 contain the amplified DNA.

For the treatment of the subsequent hybridization step, delivering carrier 16 is moved to hybridization section 4. Pipette unit 6 is allowed to suck up the amplification products from reagent container 15, and is allowed to discharge the sucked products into reagent container 20. In reagent container 20, the reagent is mixed and stirred to form mixture solutions.

FIG. 3A illustrates the above state. From this state, vertical motion stage 26 is lifted as shown in FIG. 3B, and as necessary, pressing mechanism 30 and connecting mechanism 31 are lowered. Thereby, biochemical reaction cassette 19 on tray 18 is supported at the lower side by supporting member 29 and thermal block 28 and is pressed at the upper side by pressing mechanism 30 and connecting mechanism 31 for fixation. This pressing support is explained later in detail.

Next, the mixture solutions in the reagent containers 20 are transferred by pipette unit 6 to biochemical reaction cassette 19. The temperature of the biochemical reaction cassette 19 is controlled by Peltier element 27 driven by control section (not shown in the drawing). Thereby the hybridization reaction is caused.

After the hybridization reaction, delivery section 21 is moved to the position for receiving tray 18, and vertical motion stage 26 is lowered to set tray 18 supporting biochemical reaction cassette 19 onto delivery section 21. Delivery section 21 delivers tray 18 together with biochemical reaction cassette 19 to detection section 5 as shown in FIG. 3C. Finally in detection section 5, the results of the hybridization are detected.

After the above steps, delivering carriers 10,13,16 are moved together with reagent containers 12,15,20 to the respective standby positions as shown in FIG. 1. Reagent containers 12,15,20 serve for the reagent mixing as well as the reaction, and are recovered and discarded after the respective treatment steps in a manner not shown in the drawing. If necessary, another biochemical reaction cassette 19, reagent containers 12,15,20, a specimen samples and pipette tips may be placed during the detection treatment at detection section 5 for subsequent inspection to enable parallel treatment.

In the above embodiment, all reagent containers 12,15,20 which contain the reagent preliminarily are placed on delivering carrier 10,13,16. In another embodiment, the reagent may be stored in the apparatus and be transferred to reagent containers 12,15,20 as necessary. The transfer of the reagent may be conducted by pipette or a like mechanism.

Specimen sample holder 9 or pipette tip holder 8 may be placed on the delivering carrier. Biochemical reaction cassette 19 may be placed directly on delivering carrier 16, not on tray 18. With this constitution, delivery section 21 may be constituted to deliver biochemical reaction cassettes 19 one by one to detection section 5. Otherwise delivery section 21 may supports plural biochemical reaction cassettes 19 at a time.

In the above embodiment, biochemical reaction cassette 19 is floated together with tray 18 above delivering carrier 16 during the hybridization reaction. Therefore, delivering carrier 16 may be constituted so as to be movable to some extent during the hybridization reaction without interference with thermal block 28 or supporting member 29. Thereby, reagent container 20 is made movable as necessary during the hybridization reaction to conduct additional operation such as sliding of the reagent container 20 for a pipetting operation.

EXAMPLE

An example of the temperature controller of the present invention comprising biochemical reaction cassette 19, supporting member 29, Peltier element 27, thermal block 28, pressing mechanism 30, and connecting mechanism 31 is explained in detail by reference to FIGS. 4A to 6.

FIGS. 4A to 4D illustrate a construction of a biochemical reaction cassette 19. FIG. 4A is a plan view; FIG. 4B is a sectional view taken along line 4B-4B in FIG. 4A; FIG. 4C is a sectional view taken along line 4C-4C in FIG. 4B; and FIG. 4D is a bottom view. The bottom face shown in FIG. 4D and the top face shown in FIG. 4A are counter to each other.

Biochemical reaction cassette 19 comprises base plate 33 which has a DNA probe fixed thereon capable of bonding specifically to the target nucleic acid, namely a DNA microarray; and housing 32 which encloses the microarray. When the DNA probe is brought into contact with a nucleic acid specimen solution and is brought to a prescribed temperature, the DNA probe can cause hybridization reaction. The DNA probe will form a hybrid with the target nucleic acid in the nucleic acid solution by hybridization reaction.

Base plate 33 is connected to a portion of the bottom face of housing 32. For the connection, a dent in a prescribed sectional shape is made on the connection portion of base plate 33. By the connection, reaction chamber 34 is formed on base plate 33. Glass base plate 33 has a probe fixation region not shown in the drawing in a predetermined region of the surface of the bottom of reaction chamber 34.

Reaction chamber 34 is connected to injection channel 35 and discharge channel 36 extending upward from reaction chamber 34. The injection channel 35 is also connected at the other end to liquid-holding chamber 38. Discharge channel 36 is broadened near the end of reaction chamber 34 to form buffer space 37. The other end of discharge channel 36 opposite to reaction chamber 34 is connected to waste liquid-holding chamber 39. This waste liquid-holding chamber 39 contains absorbent 40 therein to absorb and hold the waste liquid. Absorbent 40 may be made of PP (polypropylene) fibers.

On the bottom face of housing 32, a conical dent 45 is formed near the end opposite to the end portion where base plate 33 is connected. The top face of housing 32 is covered with top cover 41. Top cover 41 may be made of a plastic material. The plastic top cover 41 may be melt-bonded to housing 32 by ultrasonic melt-bonding to secure air tightness between housing 32 and top cover 41.

Top cover 41 has hole 42 for connection with liquid-holding chamber 38, and hole 43 for connection with waste liquid-holding holding chamber 39. The upper face of the top cover 40 is sealed entirely with sealing sheet 44, whereby holes 42,43 are covered. Sealing sheet 44 may be made of an aluminum foil.

Figure 5:
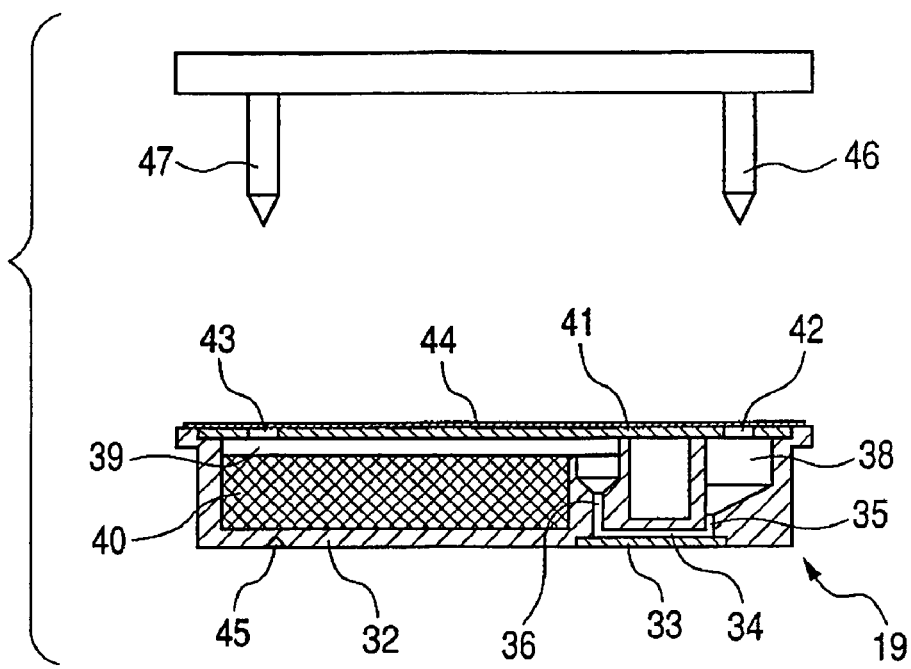
FIG. 5 illustrates a hole-boring mechanism for boring holes of a biochemical reaction cassette of FIGS. 4A to 4D.

Holes 42,43 are covered by sealing sheet 44 as shown in FIG. 4B until the start of the hybridization treatment. For the hybridization treatment, the holes are opened by boring mechanism 46,47 as shown in FIG. 5. Thereby, liquid-holding chamber 38 and waste liquid-holding chamber 39 in biochemical reaction cassette 19 are communicated with outside air through hole 42 and hole 43. Boring mechanisms 46,47, although not shown in FIG. 1 and FIGS. 3A to 3C, may be provided at a suitable position of biochemical reaction apparatus 1 together with driving mechanism thereof.

The state of connection of base plate 33 with housing 32 is not limited to that shown in the drawings. Housing 32 may be made of polycarbonate, but is not limited thereto, and may be made of glass, rubber, or silicone, a material other than polycarbonate. Base plate 33 may be made of glass, but is not limited thereto, and may be made of a plastic material, silicone, or the like.

Figure 6:
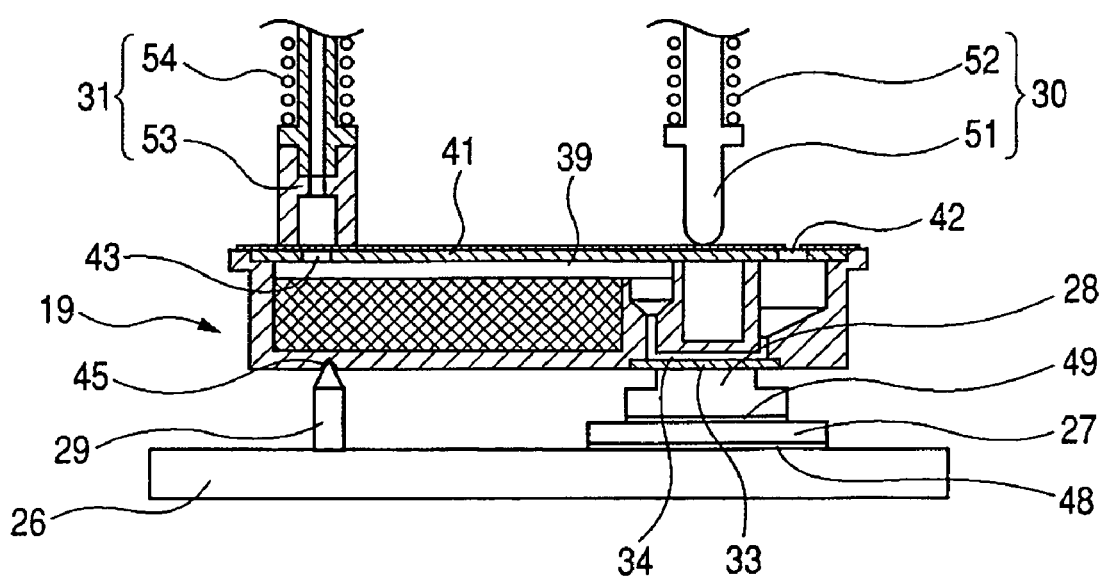
FIG. 6 illustrates a state of holding the biochemical reaction cassette of FIGS. 4A to 4D in the biochemical reaction apparatus of FIG. 1.
Figure 7:
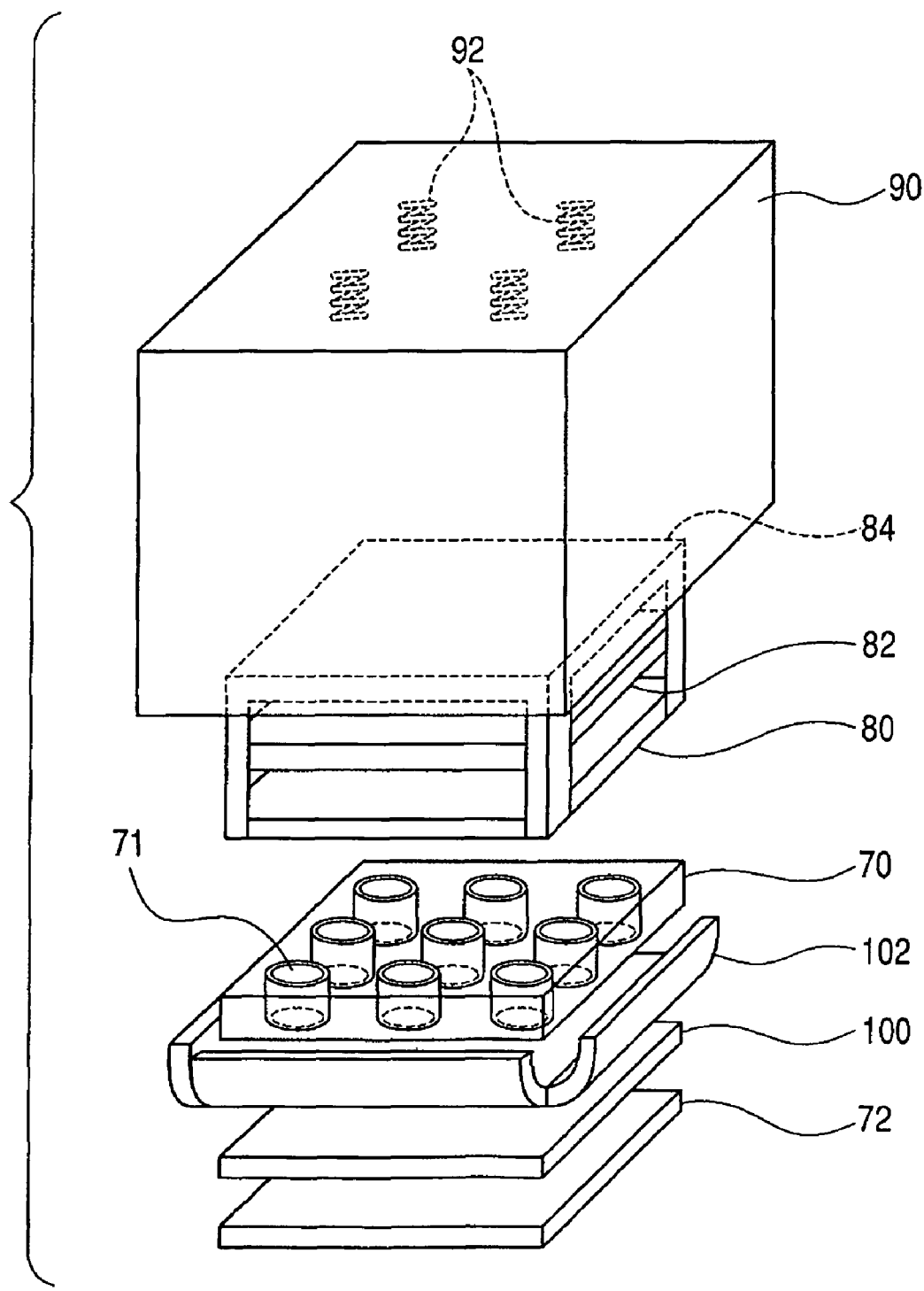
FIG. 7 illustrates a prior art technique.

In hybridization treatment, as mentioned above, biochemical reaction cassette 19 is supported by contact with thermal block 28 and supporting member 29 on the bottom face and by contact with pressing mechanism 30 and connecting mechanism 31 on the top face. FIG. 6 shows this supported state.

Thermal block 28 has a flat top face. This top face is brought into planar contact with the lower face of base plate 33 of biochemical reaction cassette 19 as shown in FIG. 6. Thermal block 28 is placed on Peltier element 27 as mentioned above. Thermo-conductive elastic sheets 48,49 are placed between vertical motion stage 26 and Peltier element 27, and between Peltier element 27 and thermal block 28.

Supporting member 29 is at the position to fit to dent 45 on the bottom face of housing 32. Supporting member 29 has a conical tip corresponding to conical dent 45. This conical tip is engaged with conical dent 45 to touch the bottom face of biochemical reaction cassette 19.

Pressing mechanism 30 has pressing bar 51 and pressing spring 52 to energize the pressing bar downward. Connecting mechanism 31 has connecting cap 53 and pressing spring 54 to energize the cap downward. Pressing bar 51 comes to be in contact with the top face of biochemical reaction cassette 19 nearly above the center of the face of the contact of thermal block 28 and base plate 33. Connecting cap 53 comes to be in contact with the top face of biochemical reaction cassette 19 nearly above supporting member 29. Connecting cap 53 is made of rubber and cylindrical in the shape, and is brought into contact with biochemical reaction cassette 19 to cover hole 43. Connecting cap 53 is connected to a pressure-applying mechanism (not shown in the drawing), of biochemical reaction apparatus 1.

In the above constitution, biochemical reaction cassette 19 is supported under pressure application by pressing springs 52,54. In this state, even when the initial set position of biochemical reaction cassette 19 is slightly deviated, biochemical reaction cassette 19 can be brought precisely to the prescribed position by engagement of conical dent 45 with supporting member 29. Further, after setting of biochemical reaction cassette 19 in the hybridization section, undesired shift of the biochemical reaction cassette 19 by unexpected vibration or impact can be prevented. For achieving the above effect, dent 45 has preferably a sectional shape having an inclined face: a conical shape as above, a truncated conical shape, or a like shape, and the tip of supporting member 29 has preferably a shape corresponding to the shape of dent 45.

Thermal block 28 is supported by interposition of elastic sheets 48,49. Therefore, the contact face is adjusted or equalized by the pressing force to follow base plate 33. Simultaneously, the other end side opposite to the position of base plate 33 of biochemical reaction cassette 19 is supported by supporting member 29 for dynamic balance. Therefore, undesired inclination of biochemical reaction cassette 19 can be prevented which may caused by unbalance of the pressing force applied between thermal block 28 and base plate 33 and the pressure applied at the side of the supporting member 29. Thereby, base plate 33 and thermal block 28 are nearly uniformly pressed to contact tightly without an interspace.

The bottom face of base plate 33, namely the bottom face of biochemical reaction cassette 19, may be stepped or curved. Dent 45 may be made on the stepped face or slightly inclined face of base plate 33. Even in such a case also, supporting member 29 comes into contact with biochemical reaction cassette 19 at a position other than the bottom face of base plate 33 to take a dynamic balance of the biochemical reaction cassette 19 to achieve stable support.

A nucleic acid sample solution to be inspected by hybridization reaction is transferred by pipette unit 6 to biochemical reaction cassette 19 supported as mentioned above. The nucleic acid sample solution is introduced through hole 42 of top cover 41 into liquid-holding chamber 38. Injection channel 35 has a sectional area made smaller than that of liquid-holding chamber 38 to serve as a flow resistance to retard spontaneous flow from liquid-holding chamber 38 into reaction chamber 34. Therefore, a negative pressure is applied through connecting cap 53 to the side of waste liquid-holding chamber 39 by a pressure-applying mechanism to fill the nucleic acid solution into reaction chamber 34 and buffer space 37. Thus reaction chamber 34 is filled with the nucleic acid sample solution without forming a bubble.

With reaction chamber 34 and buffer portion 37 filled with the nucleic acid sample solution, Peltier element 27 is driven with control to conduct heat through elastic sheet 49 and thermal block 28 to base plate 33 to control suitably the temperature of the DNA probe on base plate 33 and the nucleic acid solution in reaction chamber 34. In this example, base plate 33 and thermal block 28 can be brought in planar contact tightly without a gap to enable satisfactory heat conduction between thermal block 28 and base plate 33. Thereby the temperature of base plate 33 can be controlled precisely and uniformly throughout the entire contact face thereof.

After completion of the hybridization reaction, a negative pressure is applied again to the side of waste liquid-holding chamber 39 by the pressure-applying mechanism to allow the nucleic acid sample solution to flow into the waste liquid-holding chamber 39. Discharge channel 36 has a sectional area smaller than that of waste liquid-holding chamber 39 to serve as a flow resistance to prevent back flow of the nucleic acid sample solution into reaction chamber 34. Thereby the nucleic acid sample solution after the reaction is absorbed by absorbent 40 in waste liquid-holding chamber 39 and stored therein. Thereafter, biochemical reaction cassette 19 is delivered to detection section 5 for detection treatment as mentioned above. In this section, hybridization reaction product is detected, for example by utilizing fluorescent label as mentioned above.

In this Example, thermal block 28 is supported to be capable of changing its direction, to some extent, in contact with base plate 33 by interposition of elastic sheets 48,49. Otherwise, in place of elastic sheets 48,49, thermal block 28 may be supported by a so-called gimbal mechanism to be capable of changing its direction or equalizing. In this example, thermal block itself is rigid. Otherwise, thermal block 28 may be made of a material having high heat conductivity and being capable of elastic deformation to achieve a similar effect.

The present invention is not limited to the above embodiments and various changes and modifications can be made within the spirit and scope of the present invention. Therefore to apprise the public of the scope of the present invention, the following claims are made.

This application claims the benefit of Japanese Patent Application No. 2005-291151, filed Oct. 4, 2005, which is hereby incorporated by reference herein in its entirety.

What is claimed is:

1. A pressing and supporting mechanism comprising:
   a first structure having a chamber for causing a biochemical reaction and a first flat face formed by a base plate which forms a wall face of the chamber, wherein the base plate is a DNA microarray;
   a second structure being a member to control a temperature by conducting heat to the first structure through a contact interface to the first flat face, a second flat face of the second structure being brought into planar contact with the first flat face of the first structure, wherein a pressure is applied to the contact face to thereby support the first structure;
   a supporting means being placed at a position to fit into a dent on the plane where the first flat face is positioned, of the first structure, but not within the first flat face; and
   an energizing means including a connecting member which is a mechanism for control of a liquid flow in the first structure and energizing the first structure towards the second structure and the supporting means.

2. The pressing and supporting mechanism according to claim 1, wherein a supporting means for the second structure supports the second structure through an elastic member, so that the supporting means for the second structure supports the second structure with the capability of changing an inclination of the second flat face.

3. The pressing and supporting mechanism according to claim 1, wherein a plurality of the first structures are in planar contact with the single second structure.

4. A biochemical reaction apparatus comprising the pressing and supporting mechanism according to claim 1.

* * * * *